Figure 1:
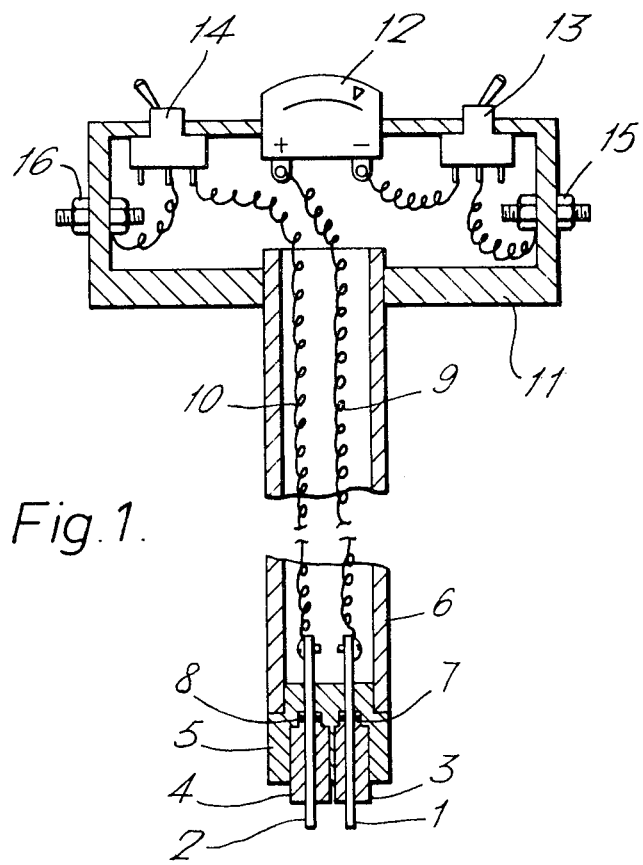

United States Patent [19]

McIvor

[11] 4,104,579
[45] Aug. 1, 1978

[54] METHOD OF EXAMINATION OF PROTECTIVE COATINGS

[75] Inventor: Malcolm Charles McIvor, Runcorn, England

[73] Assignee: Imperial Chemical Industries Limited, London, England

[21] Appl. No.: 666,933

[22] Filed: Mar. 15, 1976

[30] Foreign Application Priority Data

Mar. 27, 1975 [GB] United Kingdom ............... 12872/75

[51] Int. Cl.² ............................................ G01N 27/42
[52] U.S. Cl. ....................................... 324/29; 324/54; 324/65 CR
[58] Field of Search ...................... 324/29, 30 R, 30 B, 324/54, 29.5, 65 CR; 204/195 R

[56] References Cited

U.S. PATENT DOCUMENTS

| | | | |
|---|---|---|---|
| 2,457,234 | 12/1948 | Herbert et al. | 324/29 |
| 2,869,003 | 1/1959 | Marsh et al. | 324/29 |
| 3,250,689 | 5/1966 | Seyl | 324/65 CR |
| 3,696,017 | 10/1972 | Wallen | 204/195 F |
| 3,831,085 | 8/1974 | Kratavil | 324/54 |
| 3,858,114 | 12/1974 | Voellmin | 324/29 |
| 3,965,415 | 6/1976 | Ehret | 324/54 |

*Primary Examiner*—M. Tokar
*Attorney, Agent, or Firm*—Cushman, Darby & Cushman

[57] ABSTRACT

A method and assembly for detecting the presence of a failure in a protective coating on the surface of a metal body which comprises causing an electrolyte to make contact with the protective coating, and making comparison of the electric current generated through the electrolyte (a) between the metal body and a reference-electrode immersed in the electrolyte, and (b) between the same reference-electrode and a simulation-electrode immersed in the electrolyte and having a working surface of the same metal as that of the metal body.

13 Claims, 4 Drawing Figures

METHOD OF EXAMINATION OF PROTECTIVE COATINGS

This invention relates to a method of and a probe assembly for detecting faults in protective coatings, particularly protective coatings for metal.

Metal vessels may be protected against corrosion by their contents, by coating the interior surface of the vessels with an inert material, for example a glass, plastic or rubber. However such coatings are seldom perfect and cracks, fissures or holes in the coating allow the corrosive contents of the vessels to penetrate the coatings and cause corrosion of the metal, and ultimately produce a leak in the vessel. Moreover, protective coatings frequently become damaged or degraded during use of the vessels. It is useful to be able to detect any imperfections in the coating early enough to prevent excessive corrosion of the metal and thus prevent leakage of the contents from the vessel.

Detectors have been employed for this purpose which comprise an electrode dipping into an electrolyte contained in the vessel and being connected, via a meter, to a battery, the other pole of the battery being connected to the metal body of the vessel. If there is a fault in the protective lining of the vessel so that the electrolyte is in contact with the metal body, an electric current will flow through the system and be recorded on the meter. On the other hand, if the protective lining is free from faults so that the electrolyte is not in contact with the metal body, electric current will not flow through the system.

The disadvantage of this known detector is that it can only be employed satisfactorily for detecting faults in vessels which have no electrical connection between the metal body of the vessel and its contents. Very few vessels meet this requirement because various components, for example taps or valves seldom can be coated adequately with the protective material. Such components more often are deliberately made of a corrosion-resistant metal so that they may be in contact with both the contents of the vessel and the body of the vessel. Additionally, a common method of repairing metal vessels or damaged or imperfect linings in metal vessels is to apply a patch made of a corrosion-resistant metal (e.g. tantalum or titanium); the patch may then form an electrical connection between the vessel and its contents.

According to the present invention there is provided a method for detecting the presence of a failure in a protective coating on the surface of a metal body which comprises causing an electrolyte to make contact with the protective coating (and thereby also with the metal body if there is a failure in the coating) and making comparison of the electric current generated through the electrolyte (a) between the metal body and a reference electrode immersed in the electrolyte and (b) between the same reference electrode and a second electrode immersed in the electrolyte and having a working surface of the same metal as that of the metal body.

For convenience, the second electrode is referred to hereinafter as "the simulation electrode" and the metal whose coating is under examination as "the specific metal".

The method of this invention is particularly suited to the detection of faults in an electrically-insulating protective coating, but can also be used when the coating is electrically-conductive or semi-conductive, providing there is a significant difference between the electrochemical potentials of the metal body and the protective coating.

The reference-electrode preferably is chemically-inert to the chosen electrolyte, and should have a measurable difference in electrochemical potential from that of the specific metal whose coating is being examined. It may be made of a metal which has a very different position in the electrochemical series from the specific metal, and it is most suitably a noble metal, preferably gold or platinum.

The simulation-electrode may be made entirely of the said specific metal or it may be made of other conductive materials with an outer electrolyte-contacting layer composed of the said specific metal.

The electrolyte may be a salt, acid or base in the liquid phase, for example an aqueous solution, and mixtures of electrolytes may be used if desired.

If the coating to be tested is normally intended for use against a corrosive material which is itself an electrolyte, this corrosive material conveniently may be used as the electrolyte for the test. It is especially convenient to be able to perform the test in this way without changing the electrolyte, but a different electrolyte may be used if desired.

The electrolyte is applied over the protective-coating in the region to be tested. In practice, the electrolyte will usually be applied over the whole of the coated surface to be tested (for example by filling an internally-coated vessel to the level which corrosive material reaches during normal use of the vessel) but in cases where this is not practicable, for example because of the shape of the coated body or the presence of interfering electrically-conducting areas, the electrolyte may be applied to the specific area or areas of coating selected for testing.

The electrodes may be connected in a circuit having provision for measuring electric currents which flow in the circuit. Such a circuit will normally comprise switches and a meter, for example a microammeter.

The current generated between the reference-electrode and the simulation-electrode is monitored first as a standard current. Then the reference-electrode is connected, via the same meter, to the specific metal of the body which is coated and any current thereby generated is recorded. If this current is substantially the same as the standard current, a fault in the coating is indicated, but if the current is substantially different from the standard current, then the coating is intact.

The method of the invention can be used to detect a failure in a surface coating even when the whole of the metal body is not protectively coated, provided that the specific metal which is coated is not in direct contact with the electrolyte when the coating is intact. If there are two or more different specific metals which are coated, the method can be used to detect failure in each and it will reveal which coating has the failure. This last method would naturally involve more than two electrodes; there would be one reference-electrode and a simulation-electrode for each different specific metal which had been coated, although a common reference-electrode might be employed.

In a preferred use of the invention the metal body is a vessel, for example of steel, covered internally with an enamel or glazing as a protective coating. The vessel may be provided with fittings which interrupt the coating and electrically connect the body with the electrolyte, for example valves, taps, supports and internal patches, and the method will operate provided these fittings and patches are made of a metal other than that of the body of the vessel, or of course provided they also are covered with the protective coating. The method of the invention is of particular value when the coated vessel is designed for holding a corrosive material, for example a strong mineral acid, possibly for long periods of time. If there is a failure in the coating, for example a crack, fissure or hole, which will give access for the corrosive material to the metal body, the vessel may soon develop a hole and leak. Accordingly, before the corrosive material is allowed to remain in the vessel, the method may be used to detect whether or not the coating is intact and satisfactory. When a vessel containing corrosive material is being used, providing the material is an electrolyte the method of the invention may be used to periodically check the condition of the coating. If the test is performed often during the performance of the vessel, a fault in the coating may be detected sufficiently early to prevent severe corrosion of the vessel.

The method of the invention is of value as a maintenance tool for many different types of container or vessel, for example reactors on chemical plant, storage tanks or transport tanks on road and rail wagons, and in marine vessels.

In addition to enabling a fault in a coating to be detected, the method of the invention enables the approximate location of the fault to be determined. Once it has been established that there is a fault in the coating, electrolyte can be removed progressively from the coating until the meter registers that the coating contacted by the remaining electrolyte is intact; the fault in the coating is then known to be in the area from which electrolyte has been removed. For example, if a fault is detected in a storage tank filled with electrolyte, electrolyte can be run off from the tank so removing electrolyte from an area of the tank coating. If the meter still registers a fault in the coating, that fault is still below the level of the electrolyte in the tank. Further electrolyte is then removed, and the procedure is repeated until the meter reading indicates that the coating is intact; the fault is then known to be just above the level of the electrolyte then in the tank.

The method of the invention employs a simulation-electrode immersed in the electrolyte. In cases where the electrolyte is corrosive towards the metal body of, say, a vessel and hence towards the simulation-electrode, it will be necessary to remove this electrode from the vessel between tests. Primarily with this requirement in mind we have devised a probe assembly containing the reference-electrode and the simulation-electrode which assembly is portable and hence is readily removed from a vessel at the completion of a test. Being portable, the probe assembly can of course be moved from one vessel to another vessel as desired.

Accordingly, a further feature of the present invention is a probe assembly for detecting the presence of a failure in a protective coating on the surface of a metal vessel, comprising a first electrode (reference-electrode) having a working surface inert to electrolyte and a second electrode (simulation-electrode) having a working surface of the same metal as that of the metal vessel, the electrodes being disposed so that their working surfaces may contact simultaneously an electrolyte contained in the vessel, and an electrical circuit containing a meter and switches adapted so that the first electrode may be connected via the meter either directly to the second electrode or to the metal body of the vessel.

If more than one specific metal is present in the metal body of the vessel, the probe assembly may contain additional simulation-electrodes, in particular it may contain a simulation-electrode for each specific metal of the body. In this case, the electrical circuitry can be designed such that the meter will register the currents generated between the reference electrode and each simulation-electrode. In this way a failure in the coating allowing access of electrolyte to any one of the specific metals of the body can be detected, whereas such a failure might not be detected using a single simulation-electrode.

An advantage of the method of the invention is that it is self-checking as to the absence of a fault in the electrodes and/or the meter. Connection of the reference-electrode to the simulation-electrode when both are immersed in electrolyte will always produce a reading on the meter due to the different electrochemical potentials of the working surfaces of these electrodes. A "zero reading" therefore would represent a fault in the detector system. In a preferred embodiment of the probe assembly, provision is made for checking that the contacts with the metal body of the vessel are good. As stated hereinbefore the switches in the probe assembly are adapted to enable the reference-electrode to be connected either directly to the simulation-electrode or to the metal body of the vessel. In the preferred embodiment the switches are also adapted to enable the reference electrode to be connected to the simulation-electrode indirectly via the metal body of the vessel. If the current generated between the two electrodes is substantially the same whether they are connected directly or indirectly, then the contacts with the metal body of the vessel must be good; if they differ appreciably, and especially if the indirect connection gives a zero reading, the contacts must be bad.

It is to be understood, however, that a different meter reading between direct and indirect connections of the electrodes is to be expected in cases where the metal body of the vessel is conductively connected to the electrolyte in the vessel by fittings or patches made of a metal higher in the electrochemical series than the metal of the body of the vessel. Such fittings or patches may contribute to the current registered by the meter when the electrodes are connected indirectly through the metal body of the vessel. For example it has been found that with a mild steel vessel fitted with a stainless steel stirrer and containing 10% nitric acid, the current generated by direct connection of a platinum reference electrode to a mild steel simulation-electrode was 60$\mu$A whilst indirect connection of the two electrodes through the metal body of the vessel was 80$\mu$A. The second figure is higher than the first due to a contribution by the stainless steel stirrer, and it was subsequently confirmed that direct connection of the platinum reference-electrode to a stainless steel electrode immersed in the electrolyte was approximately 20$\mu$A. In this case a difference between the currents generated by direct and indirect connection of the reference-electrode and the simulation-electrode did not signify faulty contacts with the metal body of the vessel, and in general a higher meter reading by indirect connection rather than by direct connection of the electrodes signifies that the metal contacts with the metal body of the vessel are good.

Figure 2:
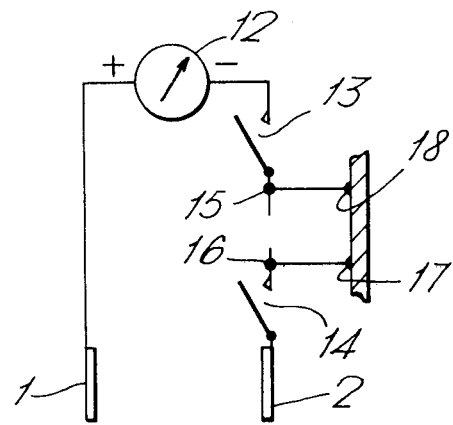
Figure 3:
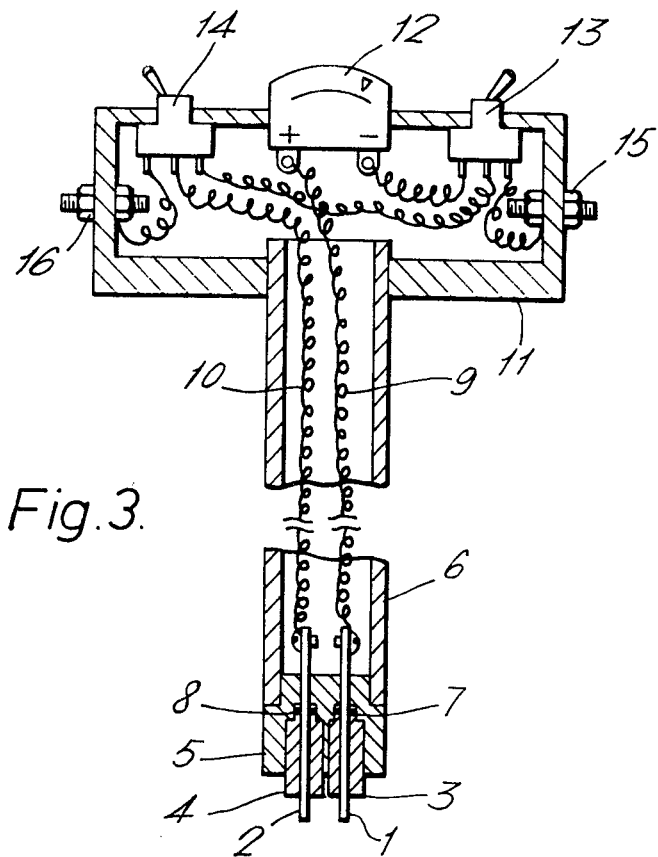
Figure 4:
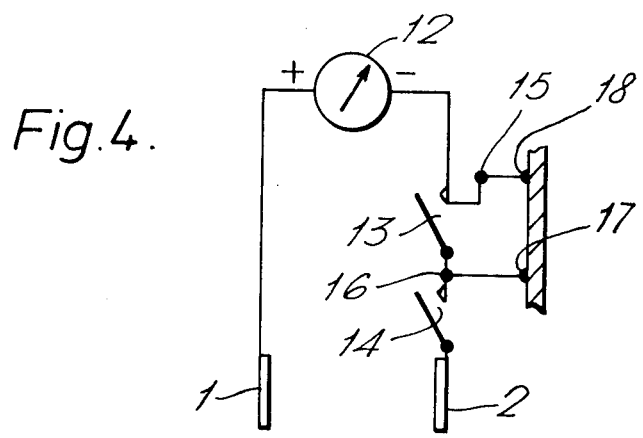

The invention will now be described by way of example only with reference to the accompanying drawings, in which:

FIG. 1 shows a sectional side elevation of a simple probe assembly according to the invention, FIG. 2 shows schematically the electrical circuitry of the probe assembly shown in FIG. 1, FIG. 3 shows a preferred embodiment of the probe assembly according to the invention, and FIG. 4 shows schematically the electrical circuitry of the probe assembly shown in FIG. 3.

Referring to FIG. 1, a thin rod of platinum 1 and similar-sized thin rod of steel 2 are each placed in electrically non-conducting sleeves 3, 4 screwed into appropriately bored parallel holes in a non-conducting bush 5 adapted to screw into the lower end of a non-conducting tube 6. The rods, which form the electrodes of the probe assembly, are retained in the bush by means of the compression of rubber O-rings 7, 8 and are connected by wires 9, 10 running along the tube 6 to the terminals of electrical components mounted on a non-conducting dish 11. The rod 1 is connected to the positive terminal of a microammeter 12 (for example an ammeter rated as 0–100μA) the negative terminal of which is connected to a switch 13. Rod 2 is connected to one side of a switch 14. Terminal connectors 15, 16 are connected with wires to switches 13 and 14 respectively, as shown in FIG. 1.

The non-conductive components apart from the rubber O-rings i.e. sleeves, bush, tube and dish are preferably all made of polytetrafluoroethylene, but other strong and chemically-inert insulators may be used, for example nylon, polypropylene, high-density polythene, and filled thermosetting resins.

The electrical circuitry of the probe assembly of FIG. 1 is illustrated in FIG. 2, which additionally shows terminal connectors 15, 16 connected to points 17, 18 on the metal body of a vessel being examined.

For use in the method of the invention the probe assembly is placed in a liquid electrolyte contained in an internally-lined steel vessel under examination so that the electrodes and part of the tube 6 are submerged in the electrolyte. Electrical connection is made between the terminal connectors 15, 16 and two points 17, 18 on the body of the steel vessel.

Switches 13 and 14 are closed (see FIG. 2), and a reading on the microammeter is taken, the value of this current being noted. This is the current generated through the electrolyte between the simulation-electrode 2 and the reference-electrode 1, the electrodes being connected indirectly via the body 1 of the vessel. That contacts 17, 18 are good is checked in this way. The switch 14 is then opened and the new reading on the microammeter taken; this gives the current generated, if any, between the reference-electrode 1 and the metal body of the steel vessel. If the value of this second current is approximately the same as that between the reference- and simulation-electrodes, the example within ±10% of the value of that current, the coating is not satisfactory; a fault in the coating exists which allows electrolyte to contact the steel body of the vessel. When the coating is providing good protection to the body of the vessel, the two current readings will be appreciably different.

Typical readings which have been recorded using the probe assembly, employing hydrochloric acid as electrolyte in a glass-lined steel vessel, when the coating is satisfactory, are 250μA for the first current and less than 40μA for the second current.

A variable shunt may be placed across the terminals of the microammeter which then may be adjusted so that the larger of the two currents causes nearly full-scale deflection of the meter.

In the preferred embodiment of probe assembly shown in FIG. 3, like parts to those in the assembly shown in FIGS. 1 and 2 are indicated by the same reference numerals. The probe assembly is essentially the same as that shown in FIG. 1, but the electrical circuitry is different. In this preferred embodiment, there is a direct link between switches 13 and 14 to enable electrodes 1 and 2 to be connected directly instead of only through the metal body of the vessel as in the assembly shown in FIGS. 1 and 2.

In using this assembly, the first meter reading is taken with the switches 13 and 14 closed so that the electrodes 1 and 2 are directly connected. Switch 13 is then opened so that the electrodes 1 and 2 are connected only indirectly via the metal body of the vessel under test. If these two readings are substantially the same, or if the second is greater than the first, then contacts 17 and 18 are good. Switch 14 is now opened so that electrode 1 is connected only with the body of the vessel under test and the new meter reading is noted. If this third reading is appreciably lower than the first reading taken, i.e. that when the electrodes 1 and 2 are directly connected, then the coating is intact; this third reading will be zero in the case of a wholly-lined vessel but will be greater than zero if the body of the vessel is electrically-connected to the electrolyte by fittings, patches or the like.

Using either of the above probe assemblies, typical meter readings in tests carried out on glass-lined mild steel vessels containing hydrochloric acid and in which the lining was intact, using a platinum reference-electrode and a mild steel simulation-electrode, are of the order of 250μA for the current generated when the electrodes 1 and 2 are directly connected, and of the order of 40μA for the current generated when the electrode 1 is connected only with the metal body of the vessel. The figure of 40μA is accounted for by the fact that the vessel was provided with a stainless steel stirrer making electrical contact between the metal body of the vessel and the electrolyte in the vessel; in the absence of such a connection, the reading should be substantially zero. When the lining of the vessel was damaged by impact, the second reading increased to the order of 250μA.

Using the probe assembly shown in FIGS. 3 and 4 on the same vessel containing 10% nitric acid, typical currents registered on the meter were (a) of the order of 60μA when the electrodes 1 and 2 were connected directly (switches 13 and 14 closed), b of the order of 80μA when switch 13 was opened, and of the order of 20μA when switch 14 was opened, showing that the lining of the vessel was intact. When the lining was damaged, the final reading increased to the order of 80μA.

What we claim is:

1. A method for detecting the presence of a failure in a protective coating on the interior surface of a metal vessel which comprises causing an electrolyte to make contact with the protective coating, and making comparison of the electric current generated through the electrolyte (a) between the metal vessel and a reference-electrode immersed in the electrolyte, and (b) between the same reference electrode and a simulation-electrode immersed in the electrolyte and having a working surface of the same metal as that of the metal vessel said reference electrode and simulation-electrode simultaneously contacting said electrolyte.

2. A method as claimed in claim 1 in which the working surface of the reference-electrode is chemically inert to the electrolyte.

3. A method as described in claim 2 in which the reference-electrode is made of a noble metal.

4. A method as claimed in claim 3 in which the noble metal is platinum.

5. A method as claimed in claim 1 for detecting the presence of a failure in a protective coating on the surface of a mild steel vessel, in which at least the working surface of the simulation-electrode is made of mild steel.

6. A method as claimed in claim 1 in which the electrolyte is an aqueous solution of an acid, base or salt.

7. A method as claimed in claim 1 wherein subsequent to detection of the presence of a failure in the protective coating, the approximate location of a failure is determined by progressively removing the electrolyte from areas of the protective coating until the comparison of electric currents indicates that a failure no longer exists in the protective coating so that the failure exists in that area of the coating from which electrolyte has been removed.

8. A probe assembly for detecting the presence of a failure in a protective coating on the surface of a metal vessel comprising a reference-electrode having a working surface chemically inert to electrolyte and a simulation-electrode having a working surface of the same metal as that of the vessel, the electrodes being disposed so that their working surfaces may contact simultaneously an electrolyte contained in the vessel, and an electrical circuit containing a meter, a switch adapted so that the reference electrode may be connected via the meter either directly to the simulation-electrode or to the metal body of the vessel.

9. A probe assembly as described in claim 8 wherein the working surface of the reference-electrode is made of a noble metal.

10. A probe assembly as claimed in claim 9 wherein the noble metal is platinum.

11. A probe assembly as claimed in claim 8 for detecting a failure in a protective coating on the surface of a vessel made of more than one metal which contains more than one simulation-electrode, each simulation-electrode having a working surface made of one of the metals of the vessel.

12. A probe assembly as claimed in claim 8 wherein the switches are adapted so that the reference-electrode may also be connected indirectly to the simulation-electrode via the metal body of the vessel.

13. A probe assembly as claimed in claim 8 for detecting the presence of a failure in a protective coating on the surface of a mild steel vessel wherein the working surface of the simulation-electrode is made of mild steel.

* * * * *